United States Patent
Harada et al.

(10) Patent No.: US 7,396,928 B2
(45) Date of Patent: Jul. 8, 2008

(54) CRYSTALS OF 5-[2-AMINO-4-(2-FURYL) PYRIMIDIN-5-YL]-1-METHYLPYRIDIN-2 (1H)-ONE AND PROCESSES FOR PREPARING THE SAME

(75) Inventors: Hitoshi Harada, Tsukuba (JP); Hiroshi Ishihara, Tsukuba (JP); Yoshiaki Sato, Tsukuba (JP); Hiroyuki Chiba, Kamisu (JP); Teiji Takigawa, Kamisu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 142 days.

(21) Appl. No.: 11/378,315

(22) Filed: Mar. 20, 2006

(65) Prior Publication Data

US 2006/0235225 A1    Oct. 19, 2006

Related U.S. Application Data

(60) Provisional application No. 60/663,580, filed on Mar. 21, 2005.

(51) Int. Cl.
*C07D 401/04*    (2006.01)
(52) U.S. Cl. .................................................... 544/331

(58) Field of Classification Search ................... 544/331
See application file for complete search history.

(56) References Cited

U.S. PATENT DOCUMENTS

2005/0004149 A1 * 1/2005 Harada et al. ............... 514/275

FOREIGN PATENT DOCUMENTS

| EP | 1439175 A1 | 7/2004 |
|---|---|---|
| WO | WO-03/035639 A1 | 5/2003 |

OTHER PUBLICATIONS

Fischer et al., J. Org. Chem., vol. 52, pp. 564-569, (1987).
Selvamurugan et al., Tetrahedron, vol. 57, pp. 6065-6069, (2001).

* cited by examiner

*Primary Examiner*—Deepak Rao
(74) *Attorney, Agent, or Firm*—Birch, Stewart, Kolasch & Birch, LLP (57) ABSTRACT

Crystals of 5-[2-amino-4-(2-furyl)pyrimidin-5-yl]-1-methylpyridin-2(1H)-one having a diffraction peak at a diffraction angle (2θ±0.2°) of 12.8°, 18.1° and/or 23.5° in a powder X-ray diffraction are excellent in stability against light, therefore are suitable for an active ingredient of a preventing and therapeutic agent for diseases such as constipation.

4 Claims, 11 Drawing Sheets

CRYSTALS OF 5-[2-AMINO-4-(2-FURYL) PYRIMIDIN-5-YL]-1-METHYLPYRIDIN-2 (1H)-ONE AND PROCESSES FOR PREPARING THE SAME

CROSS-REFERENCE TO RELATED APPLICATIONS

This application claims priority to a provisional application No. 60/663,580 filed on Mar. 21, 2005 by the same Applicant, which is hereby incorporated by reference in its entirety.

BACKGROUND OF THE INVENTION

1. Field of the Invention

The present invention relates to crystals (crystal form A) of 5-[2-amino-4-(2-furyl)pyrimidin-5-yl]-1-methylpyridin-2 (1H)-one, a compound effective for prevention and treatment for various diseases such as constipation, and processes for preparing the same.

2. Related Background of the Invention

5-[2-Amino-4-(2-furyl)pyrimidin-5-yl]-1-methylpyridin-2(1H)-one is a compound having adenosine receptor antagonism and being effective for prevention and treatment for various diseases such as constipation (see patent document 1). Patent document 1, Example 16 discloses 5-[2-amino-4-(2-furyl)pyrimidin-5-yl]-1-methylpyridin-2(1H)-one was obtained as crystals.

Patent document 1: WO 03/035639

SUMMARY OF THE INVENTION

The active ingredient of a drug must be stably supplied as a product of consistent quality. Therefore, when the active ingredient of a drug is obtained as a crystalline substance, it preferably consists of a homogenous crystal form with suitable physical properties such as being stable against light. Therefore the object of the present invention is to provide crystals of 5-[2-amino-4-(2-furyl)pyrimidin-5-yl]-1-methylpyridin-2(1H)-one having suitable physical properties.

As a result of much avid research, the present inventors have discovered novel crystals of 5-[2-amino-4-(2-furyl)pyrimidin-5-yl]-1-methylpyridin-2(1H)-one (hereinafter referred to as the crystal form A) which have different crystal structure from the crystals disclosed in patent document 1 (hereinafter referred to as the crystal form B) and are more stable against light than the crystal form B, and have succeeded in completing this invention.

Specifically, the present invention provides the following [1] to [3].

[1] a crystal of 5-[2-amino-4-(2-furyl)pyrimidin-5-yl]-1-methylpyridin-2(1H)-one having a diffraction peak at a diffraction angle (2θ±0.2°) of 12.8°, 18.1° and/or 23.5° in a powder X-ray diffraction.

[2] a crystal of 5-[2-amino-4-(2-furyl)pyrimidin-5-yl]-1-methylpyridin-2(1H)-one having a peak at a chemical shift of approximately 113.1 ppm and/or approximately 140.8 ppm in a $^{13}C$ solid state nuclear magnetic resonance spectrum (hereinafter referred to as $^{13}C$ solid state NMR spectrum).

[3] a process for preparing a crystal according to [1] or [2], characterized by that 5-[2-amino-4-(2-furyl)pyrimidin-5-yl]-1-methylpyridin-2(1H)-one is heated and dissolved in a solvent and then crystallized by gradual cooling.

The crystal form A of the invention has suitable physical properties such as being stable against exposure to light, and is suitable for using as an active ingredient of a preventing and therapeutic agent for diseases such as constipation.

DESCRIPTION OF THE PREFERRED EMBODIMENTS

Crystal Form A

Figure 1:
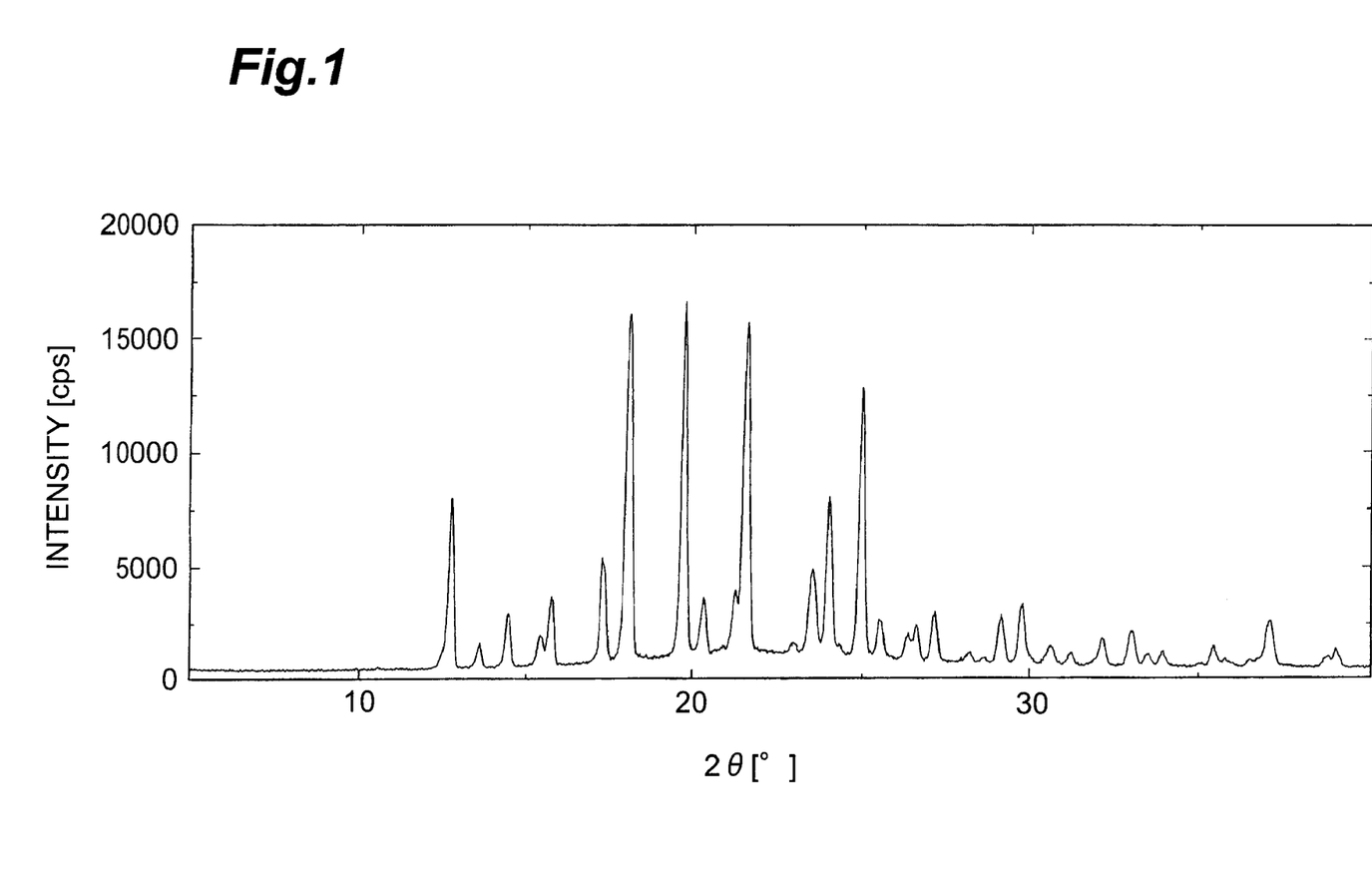
FIG. 1 is a drawing representing a powder X-ray diffraction pattern of the crystals obtained in Example 1.
Figure 8:
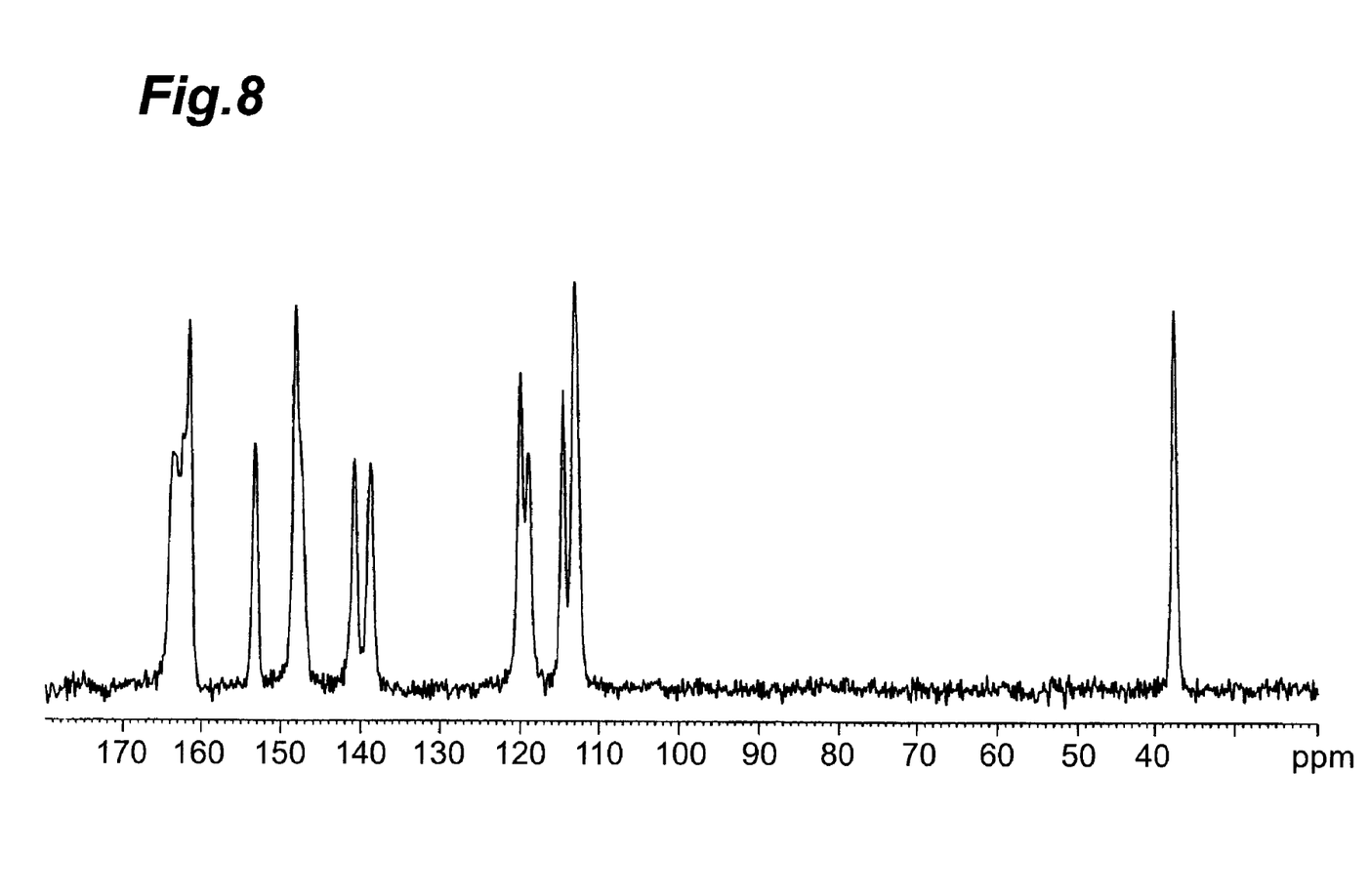
FIG. 8 is a drawing representing a $^{13}C$ solid state NMR spectrum of the crystals obtained in Example 1.
Figure 10:
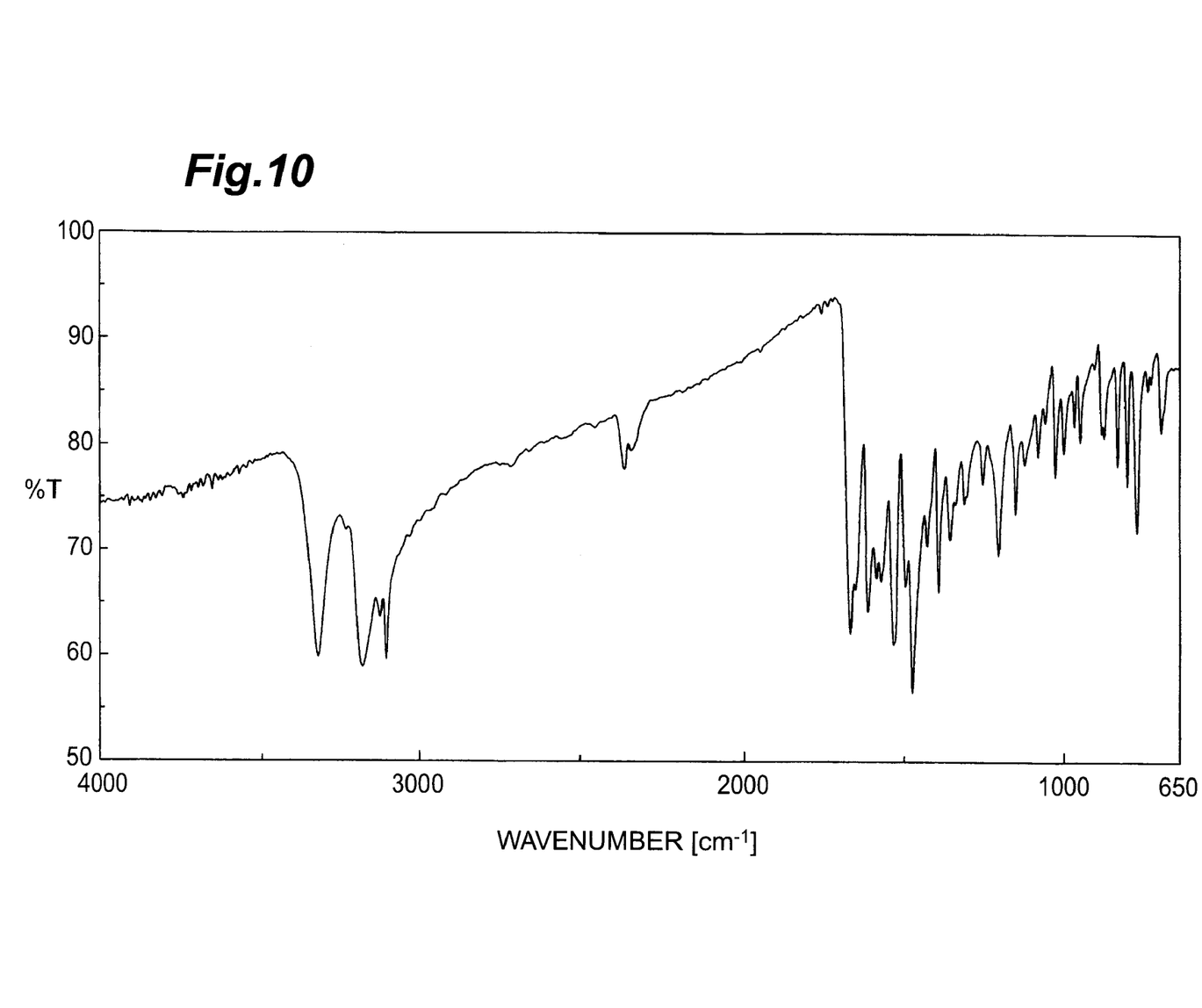
FIG. 10 is a drawing representing an infrared absorption spectrum of the crystals obtained in Example 1.

The crystals (the crystal form A) of 5-[2-amino-4-(2-furyl)pyrimidin-5-yl]-1-methylpyridin-2(1H)-one according to the invention are characterized by having a diffraction peak at a diffraction angle (2θ±0.2°) of 12.8°, 18.1° and/or 23.5° in a powder X-ray diffraction and characterized by having a peak at a chemical shift of approximately 113.1 ppm and/or approximately 140.8 ppm in a $^{13}C$ solid-state NMR spectrum. These characteristic peaks in a powder X-ray diffraction and a $^{13}C$ solid-state NMR spectrum are not observed for the crystals disclosed in patent document 1, example 16 (the crystal form B). Typical powder X-ray diffraction pattern and $^{13}C$ solid-state NMR spectrum of the crystal form A are shown in FIG. 1 and FIG. 8, respectively. A typical infrared absorption spectrum for the crystal form A is shown in FIG. 10. The crystal form A is more stable against exposure to light than the crystal form B.

Since the diffraction angle (2θ) in a powder X-ray diffraction generally has a diffraction angle error in the range of ±0.2°, the aforementioned values for the diffraction angle must be interpreted as including values within a range of ±0.2°. Thus, the present invention encompasses not only crystals whose peak diffraction angle in a powder X-ray diffraction matches exactly, but also crystals whose peak diffraction angle matches with an error of ±0.2°.

Specifically, throughout the present specification, "having a diffraction peak at a diffraction angle (2θ±0.2°) of 12.8°" means "having a diffraction peak at a diffraction angle (2θ) in the range of 12.6°-13.0°", "having a diffraction peak at a diffraction angle (2θ±0.2°) of 18.1°" means "having a diffraction peak at a diffraction angle (2θ) in the range of 17.9°-18.3°", and "having a diffraction peak at a diffraction angle (2θ±0.2°) of 23.5°" means "having a diffraction peak at a diffraction angle (2θ) in the range of 23.3°-23.7°". "Having a diffraction peak at a diffraction angle (2θ±0.2°) of 12.8°, 18.1° and/or 23.5°'" means having at least one of the above diffraction peaks.

Throughout the present specification, "having a peak at a chemical shift of approximately 113.1 ppm" means "having a peak substantially equivalent to a chemical shift of 113.1 ppm, when a $^{13}C$ solid state NMR spectrum is measured under ordinary measuring conditions", and "having a peak at a chemical shift of approximately 140.8 ppm" means "having a peak substantially equivalent to a chemical shift of 140.8 ppm, when a $^{13}C$ solid state NMR spectrum is measured under ordinary measuring conditions". "Having a peak at a chemical shift of approximately 113.1 ppm and/or approximately 140.8 ppm" means having at least one of the above peaks.

Process for Preparing the Crystal Form A

The process for preparing the crystal form A of the invention is characterized by that 5-[2-amino-4-(2-furyl)pyrimidin-5-yl]-1-methylpyridin-2(1H)-one is heated and dissolved in a solvent and then crystallized by gradual cooling. 5-[2-Amino-4-(2-furyl)pyrimidin-5-yl]-1-methylpyridin-2(1H)-one used for crystallization may be in any form. That is, it may be a hydrate or anhydrate, amorphous or crystalline (including combinations of multiple crystal forms) compound, or a mixture thereof. 5-[2-Amino-4-(2-furyl)pyrimidin-5-yl]-1-methylpyridin-2(1H)-one can be prepared by the method disclosed in patent document 1, and also by the method described in Preparation Examples 1 to 6 below.

The solvent used for crystallization is not restricted so long as it dissolves starting materials to some extent, and is for example a single solvent or a mixed solvent of two or more selected from a group consisting of an alcoholic solvent such as methanol, ethanol and propanol, dimethylsulfoxide (hereinafter referred to as "DMSO") and water. Preferred solvents are a single solvent of an alcoholic solvent, a single solvent of DMSO, a mixed solvent of water and an alcoholic solvent or a mixed solvent of water and DMSO.

The amount of solvent used may be appropriately selected between the minimum amount in which 5-[2-amino-4-(2-furyl)pyrimidin-5-yl]-1-methylpyridin-2(1H)-one will dissolve by heating and the maximum amount at which the yield of the crystals is not significantly reduced, and it is preferably a 8-30 fold amount, in terms of the volume ratio with respect to the weight of 5-[2-amino-4-(2-furyl)pyrimidin-5-yl]-1-methylpyridin-2(1H)-one.

The temperature for dissolution of 5-[2-amino-4-(2-furyl)pyrimidin-5-yl]-1-methylpyridin-2(1H)-one may be appropriately selected depending on the solvent, but it is preferably from 70° C. to heating reflux temperature. The gradual cooling during crystallization is preferably carried out while suitably adjusting the cooling rate in consideration of the effect on quality and particle size of the crystals, preferable rate is 10° C. to 30° C./hr or slower, more preferable rate is 5° C. to 10° C./hr or slower and the most preferable rate is 5° C./hr or slower.

The precipitated crystals may be separated by an ordinary filtration procedure, washed with an appropriate solvent if necessary, and then dried to afford the desired crystals. The solvent used for washing of the crystals is generally the same as the crystallization solvent. The crystals can be dried by merely standing in air or by heating. The drying may be carried out under airflow or under reduced pressure.

Pharmaceutical Composition Comprising the Crystal Form A

The use of 5-[2-amino-4-(2-furyl)pyrimidin-5-yl]-1-methylpyridin-2(1H)-one as a therapeutic agent for constipation is disclosed in detail in patent document 1, and the crystal form A may be used in a similar fashion as the active ingredient of a therapeutic agent for constipation. The entirety of the disclosure of patent document 1 is incorporated by reference into the disclosure of the present specification. Moreover, the crystal form A has satisfactory stability and physical properties and are hence the most suitable form for use of 5-[2-amino-4-(2-furyl)pyrimidin-5-yl]-1-methylpyridin-2(1H)-one as the active ingredient of a therapeutic agent for constipation.

The crystal form A may be formulated by an ordinary method into tablets, powder, fine powder, granules, coated tablets, capsules, syrup, lozenges, an inhalant, suppository, injection, ointment, eye ointment, eye drop, nose drop, ear drop, pap, lotion or the like. For formulation there may be employed commonly used excipients, binders, lubricants, coloring agents, taste correctives and, if necessary, stabilizers, emulsifiers, absorption accelerators, surfactants, pH adjustors, antiseptics, antioxidants and the like, while other components ordinarily used as raw materials for drug formulation may also be added according to common procedures.

As examples of such components there may be mentioned animal or vegetable oils such as soybean oil, beef tallow and synthetic glycerides; hydrocarbons such as liquid paraffin, squalene and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid ester, sorbitan fatty acid ester, glycerin fatty acid ester, polyoxyethylenesorbitan fatty acid ester, polyoxyethylene hydrogenated castor oil and polyoxyethylene-polyoxypropylene block copolymer; water-soluble polymers such as hydroxyethylcellulose, polyacrylic acid, carboxyvinyl polymer, polyethylene glycol, polyvinylpyrrolidone and methylcellulose; lower alcohols such as ethanol and isopropyl alcohol; polyhydric alcohols such as glycerin, propylene glycol, dipropylene glycol and sorbitol; sugars such as glucose and sucrose; inorganic powders such as silicic anhydride, magnesium aluminum silicate and aluminum silicate, purified water, and the like.

As examples of excipients there may be mentioned lactose, corn starch, white soft sugar, glucose, mannitol, sorbit, crystalline cellulose, silicon dioxide and the like, as examples of binders there may be mentioned polyvinyl alcohol, polyvinyl ether, methylcellulose, ethylcellulose, gum Arabic, tragacanth gum, gelatin, shellac, hydroxypropylmethylcellulose, hydroxypropylcellulose, polyvinylpyrrolidone, polypropylene glycol-polyoxyethylene block polymer, meglumine and the like, as examples of disintegrators there may be mentioned starch, agar, gelatin powder, crystalline cellulose, calcium carbonate, sodium hydrogencarbonate, calcium citrate, dextrin, pectin, carboxymethylcellulose calcium and the like, as examples of lubricants there may be mentioned magnesium stearate, talc, polyethylene glycol, silica, hydrogenated vegetable oils and the like, as examples of coloring agents there may be mentioned those approved for addition to pharmaceuticals, and as examples of taste correctives there may be mentioned cocoa powder, menthol, aromatic powder, peppermint oil, camphor, cinnamon powder and the like.

For production of an oral preparation, the crystal form A may be combined with an excipient and, if necessary, a binder, disintegrator, lubricant, coloring agent, taste corrective or the like and then made into a powder, fine powder, granules, tablets, coated tablets or capsules.

Also, there is no restriction against sugar-coating and, if necessary, other appropriate coating of the tablets or granules.

For production of a liquid preparation such as a syrup or pharmaceutical preparation for injection, the crystal form A may be combined with a pH adjustor, solubilizer, isotonizing agent or the like, and if necessary, with a dissolving aid, stabilizers or the like, and formulated by an ordinary method.

The method of producing an external preparation is not particularly restricted, and may be according to an ordinary method. Specifically, as base materials for pharmaceutical preparation there may be used various materials ordinarily employed for pharmaceuticals, quasi drugs, cosmetics and the like. As examples of specific base materials to be used there may be mentioned materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, and if necessary there may also be added pH adjustors, antioxidants, chelating agents, antiseptic/mildew resistant agents, coloring agents, aromatics and the like, although base materials for an external preparation of the invention are not limited to these. If necessary there may also be included components such as circulation promoters, bactericidal agents, antiflash agents, cell activators, vitamins, amino acids, humectants, keratolytic agents and the like. The amounts of such base materials are the amounts which give concentrations indicated for production of ordinary external preparations.

The form of administration of the crystal from A is not particularly restricted, and may be oral administration or parenteral administration by an ordinarily employed method. For example, the crystals may be administered after formulation into tablets, powder, granules, capsules, syrup, lozenges, an inhalant, suppository, injection, ointment, eye ointment, eye drop, nose drop, ear drop, pap, lotion or the like. The dosage of a pharmaceutical according to the invention may be appropriately selected depending on patient age, gender, body weight, severity of symptoms, particular type of condition, and on the type of dosage form or salt. For example, it will generally be administered once or divided over several times at about 30 μg to 10 g, preferably 100 μg to 5 g, more preferably 100 μg to 100 mg per day for adults in the case of oral administration or 30 μg to 1 g, preferably 100 μg to 500 mg, more preferably 100 μg to 30 mg per day in the case of injection administered once or divided over several times a day.

EXAMPLES

Preparation Example 1

Synthesis of (6-methoxypyridin-3-yl)methanol (2)

To a solution of methyl-6-methoxynicotinate (1) (650 g, 3.89 mol) in t-butyl methyl ether (hereinafter abbreviated as "MTBE") (6.5 L) cooled in an ice bath was added sodium bis(2-methoxyethoxy)aluminum hydride (65% solution in toluene, 1.45 kg, 4.67 mol) under a nitrogen atmosphere over a period of 1.3 hours. After stirring for 20 minutes, a 3.5 N aqueous solution of sodium hydroxide (2.6 L) was added to the reaction mixture while keeping the temperature 15° C. or below. The reaction mixture was stirred at 32° C. for 45 minutes and then the organic layer was separated and the aqueous layer was re-extracted with MTBE (2.3 L). The organic layers were combined and concentrated under reduced pressure to dryness, and then toluene (1.3 L) was added to the residue and azeotropic distillation was carried out. Azeotropic distillation with toluene (1.3 L) was repeated three times to give 597 g of the title compound as a pale yellow oil (yield 100%).

$^1$H-NMR (CDCl$_3$) δ (ppm): 8.11 (1H, d, J=2.4 Hz), 7.62 (1H, dd, J=2.4 Hz, 8.8 Hz), 6.75 (1H, d, J=8.8 Hz), 4.62 (2H, s), 3.93 (3H, s)

Preparation Example 2

Synthesis of 5-chloromethyl-2-methoxypyridine (3)

To a solution of (6-methoxypyridin-3-yl)methanol (2) (537.8 g, 3.86 mol) obtained in Preparation Example 1 in dimethylformamide (1.6 L) was added dropwise thionyl chloride (310 mL, 4.25 mol) over a period of 1.3 hours while cooling in an ice bath under a nitrogen atmosphere. After stirring for 1 hour while cooling in an ice bath, toluene (5.4 L) and a 2N aqueous solution of sodium hydroxide (5.4 L) were added successively to the reaction mixture at 23° C. or below. The reaction mixture was stirred for about 10 minutes and then the aqueous layer was separated, the organic layer was washed with water (2.7 L). The organic layer was concentrated under reduced pressure to dryness, and then toluene (1.0 L) was added to the residue and azeotropic distillation was carried out to give 618.8 g of the title compound as a pale yellow oil (content 556.3 g, yield 91.4%).

$^1$H-NMR (CDCl$_3$) δ (ppm): 8.15 (1H, d, J=2.4 Hz), 7.63 (1H, dd, J=2.4 Hz, 8.4 Hz), 6.75 (1H, d, J=8.4 Hz), 4.55 (2H, s), 3.94 (3H, s)

Preparation Example 3

Synthesis of furan-2-yl-morpholin-4-yl-acetonitrile (5)

A solution of furfural (4) (550 g, 5.72 mol) in toluene (5.5 L) was cooled to 8° C., and then an aqueous solution (1.1 L water) of potassium cyanide (384.6 g, 5.72 mol) was added over a period of 7 minutes.

Then, to the reaction mixture was added an aqueous solution (1.65 L water) of p-toluenesulfonic acid monohydrate (1143.0 g, 6.01 mol) over a period of 20 minutes, and the reaction mixture was further stirred for 1 hour. To the reaction mixture was added a solution of morpholine (997 g, 11.45 mol) in toluene (100 mL) over a period of 8 minutes, followed by stirring for 2.5 hours in a water bath at 20° C. The aqueous layer was separated, and the organic layer was washed with water (2.75 L) and then concentrated under reduced pressure to dryness to give 1028.7 g of the title compound as a reddish-brown oil (content 90.2%, yield 84.3%).

$^1$H-NMR (CDCl$_3$) δ (ppm): 7.47 (1H, brs), 6.57 (1H, d, J=3.2 Hz), 6.41 (1H, dd, J=3.2 Hz, 1.6 Hz), 4.85 (1H, s), 4.43 (4H, m), 4.31 (4H, m)

Preparation Example 4

Synthesis of 1-furan-2-yl-2-(6-methoxy-pyridin-3-yl)-ethanone (7)

A solution of furan-2-yl-morpholin-4-yl-acetonitrile (5) (818.0 g, content 737.9 g, 3.84 mol) obtained in Preparation Example 3 and 5-chloromethyl-2-methoxypyridine (3) (611.8 g, content 550.0 g, 3.49 mol) obtained in Preparation Example 2 in toluene (4.4 L) was cooled to −15° C., and then a solution of potassium-t-butoxide (508.9 g, 4.54 mol) in tetrahydrofuran (4.4 L) was added at −5° C. or below over a period of 72 minutes, and the reaction mixture was further stirred for 1.5 hours.

Next, to the reaction mixture was added a 6N aqueous solution of hydrochloric acid (4.4 L), followed by heating to 70° C. and stirring for 2 hours. The reaction mixture was cooled to 5° C. and a 3N aqueous solution of sodium hydroxide (3.0 L) was added at 20° C. or below. The organic layer was separated, the aqueous layer was re-extracted with toluene (6.0 L), and the organic layers were combined and concentrated under reduced pressure to dryness to give 828.5 g of the title compound as a brown oil (content 647.8 g, yield 85.5%).

2-Furan-2-yl-3-(6-methoxy-pyridin-3-yl)-2-morpholin-4-yl-propionate (6)

$^1$H-NMR (CDCl$_3$) δ (ppm): 7.71 (1H, d, J=2.4 Hz), 7.48 (1H, d, J=1.6 Hz), 7.11 (1H, dd, J=2.4 Hz, 8.4 Hz), 6.56 (1H, d, J=8.4 Hz), 6.27 (2H, m), 3.87 (3H, s), 3.80 (4H, m), 3.38 (1H, d, J=13.2), 3.26 (1H, d, J=13.2), 2.78-2.81 (2H, m), 2.45-2.78 (2H, m)

1-Furan-2-yl-2-(6-methoxy-pyridin-3-yl)-ethanone (7)

$^1$H-NMR (CDCl$_3$) δ (ppm): 8.08 (1H, d, J=2.4 Hz), 7.61 (1H, d, J=1.7 Hz), 7.53 (1H, dd, J=2.4 Hz, 8.2 Hz), 7.24 (1H, d, J=3.6 Hz), 6.71 (1H, d, J=8.2 Hz), 6.55 (1H, dd, J=1.7 Hz, 3.6 Hz), 4.05 (2H, s), 3.91 (3H, s)

Preparation Example 5

Synthesis of 5-(2-furan-2-yl-2-oxo-ethyl)-1-methyl-1H-pyridin-2-one (8)

To a solution of 1-furan-2-yl-2-(6-methoxy-pyridin-3-yl)-ethanone (7) (800.0 g, content 625.6 g, 2.88 mol) obtained in Preparation Example 4 in N-methyl-2-pyrrolidine (NMP) (1.88 L) was added iodomethane (122.6 g, 0.86 mol), and the reaction mixture was stirred at 100° C. for 3 hours and then at room temperature for 17.5 hours. To the reaction mixture was added dropwise MTBE (6.6 L) over a period of 77 minutes, followed by stirring for 1 hour while cooling in an ice bath. The precipitated crystals were collected by filtration and washed with MTBE (2.0 L), and then dried under reduced pressure at 50° C. for 3 hours to give 692.0 g of a crude product of the title compound as a dark brown powder (content 536.4 g, yield 85.7%).

To the obtained crude product (682.0 g, content 528.7 g, 2.43 mol) were added 1,2-dimethoxyethane (hereinafter abbreviated as "DME") (7.93 L) and water (0.68 L), followed by heating and stirring at 80° C. for 75 minutes. After confirming dissolution, stirring was continued overnight at 8° C. The precipitated crystals were collected by filtration and washed with DME (2.0 L), and then air-dried at 60° C. for 2.3 hours to give 468.46 g of the title compound as pale yellow crystals (content 462.8 g, yield 87.5%).

$^1$H-NMR (DMSO) δ (ppm): 8.02 (1H, d, J=1.6 Hz), 7.57 (2H, m), 7.30 (1H, dd, J=3.4 Hz, 9.2 Hz), 6.74 (1H, dd, J=1.6 Hz, 3.6 Hz), 6.33 (1H, d, J=9.2 Hz), 3.98 (2H, s), 3.38 (3H, s)

Preparation Example 6A

Synthesis of 5-[2-amino-4-(2-furyl)pyrimidin-5-yl]-1-methylpyridin-2(1H)-one (10)

To 5-(2-furan-2-yl-2-oxo-ethyl)-1-methyl-1H-pyridin-2-one (8) (402.0 g, content 397.6 g, 1.83 mol) obtained in Preparation Example 5 were added dimethylformamide (0.4 L) and N,N-dimethylformamide dimethyl acetal (654.4 g, 5.49 mol), and the reaction mixture was stirred at 60° C. for 10.5 hours and then at room temperature for 13.5 hours. To the reaction mixture were added guanidine hydrochloride (524.56 g, 5.49 mol) and 1,8-diazabicyclo[5.4.0]undec-7-en (DBU) (821 mL, 5.49 mol), and the reaction mixture was stirred for 7.8 hours at 70° C. Next, to the reaction mixture was added 2-propanol (12.0 L), followed by stirring for 2 hours in an ice bath. The precipitated crystals were collected by filtration, washed with 2-propanol (1.0 L), and then air-dried at 60° C. for 13 hours to give 424.9 g of the title compound as pale yellow crystals (content 413.0 g, yield 84.1%).

5-[2-Dimethylamino-1-(furan-2-carbonyl)-vinyl]-1-methyl-1H-pyridin-2-one (9)

$^1$H-NMR (CDCl$_3$) δ (ppm): 7.77 (1H, s), 7.45 (1H, d, J=2.0 Hz), 7.26 (1H, dd, J=2.4 Hz, 9.2 Hz), 7.14 (1H, d, J=2.4 Hz), 6.60 (1H, d, J=9.2 Hz), 6.50 (1H, d, J=3.2 Hz), 6.37 (1H, d, J=3.2 Hz), 3.55 (3H, s), 2.93 (6H, brs)

5-[2-Amino-4-(2-furyl)pyrimidin-5-yl]-1-methylpyridin-2(1H)-one (10)

$^1$H-NMR (DMSO) δ (ppm): 8.13 (1H, s), 7.75 (1H, dd, J=0.7 Hz, 1.4 Hz), 7.72 (1H, d, J=2.4 Hz), 7.20 (1H, dd, J=2.4 Hz, 9.0 Hz), 6.78 (2H, brs), 6.72 (1H, d, J=3.5 Hz), 6.56 (1H, m), 6.36 (1H, d, J=9.0 Hz), 3.44 (3H, s)

Preparation Example 6B

Synthesis of 5-[2-amino-4-(2-furyl)pyrimidin-5-yl]-1-methylpyridin-2(1H)-one (10)

To 5-(2-furan-2-yl-2-oxo-ethyl)-1-methyl-1H-pyridin-2-one (8) (10.0 g, 46.04 mmol) obtained in Preparation Example 5 were added dimethylformamide (20 mL), N,N-dimethylformamide dimethyl acetal (9.21 mL, 69.06 mmol) and DBU (10.3 mL, 69.06 mmol), and the reaction mixture was stirred at 80° C. for about 5 hours and then allowed to cool. Next, to the reaction mixture was added 2-propanol (100 mL), and the reaction mixture was stirred at 8° C. for about 16 hours. The precipitated crystals were collected by filtration, washed with 2-propanol (45 mL), and then air-dried at 50° C. for 20 minutes to give 10.2 g of a crude product of the title compound (10) as pale yellow crystals (content 10.2 g, yield 82.3%).

Example 1

Preparation of the Crystal Form A (1)

To 30 g of crude 5-[2-amino-4-(2-furyl)pyrimidin-5-yl]-1-methylpyridin-2(1H)-one (10) obtained in Preparation Example 6A were added 30 mL of 2-propanol and 150 mL of water, followed by heating and stirring for 25 minutes in an oil bath at 90° C. Upon confirming the absence of solid, filtration with heating was performed and the filtrate was heated and stirred at 70° C. for about 30 minutes. It was then heated and stirred for 1.3 hours at an external temperature of 55° C., and subsequently stirred for 2.3 hours at an external temperature of 45 to 40° C. Precipitation of crystals was confirmed at an internal temperature of approximately 47° C. The reaction mixture was further stirred at 30° C. for about 40 minutes, at room temperature for 1 hour and at 4° C. for 1.6 hours, and then the crystals were collected by filtration. The crystals were washed 3 times with 20 mL of 2-propanol and dried at 60° C. for 10.5 hours to give 19.9 g of the crystal form A.

Example 2

Preparation of the Crystal Form A (2)

To 5.0 g of crude 5-[2-amino-4-(2-furyl)pyrimidin-5-yl]-1-methylpyridin-2(1H)-one (10) obtained in Preparation Example 6A were added 50 mL of 2-propanol and 25 mL of water, and the reaction mixture was heated and stirred at 80° C. for 1 hour 15 minutes. Upon confirming the absence of solid, the reaction mixture was heated and stirred at 65° C. for about 35 minutes. It was then heated and stirred for 30 minutes at an external temperature of 55° C., and small amount of seed crystals (the crystal form A) was added, followed by stirring for 1 hour. The reaction mixture was further stirred at 50° C. for 1 hour, at 40° C. for 1 hour and at 30° C. for 1 hour, and then the crystals were collected by filtration. The crystals were dried at 50° C. for 1 hour to give 4.33 g of crystal form A (crystallization yield 86.6%).

Example 3

Preparation of the Crystal Form A (3)

In a 10 L four-neck flask were placed 360.1 g of crude 5-[2-amino-4-(2-furyl)pyrimidin-5-yl]-1-methylpyridin-2 (1H)-one (10) and a mixture (4.7 L) of 2-propanol/water (2:1), followed by stirring at 80° C. for 1.6 hours. Upon confirming the absence of solid, filtration with heating was performed. The 10 L four-neck flask was washed with a mixture (0.4 L) of 2-propanol/water (2:1) and the washings were heated at 80° C., filtered with heating and combined with the previous filtrate. The filtrate was heated at 80° C. for about 40 minutes, then gradually cooled down to approximately 39° C. over a period of about 2.2 hours to appear crystals. After further stirring for about 0.8 hours at an external temperature of 35° C., a portion of the suspension was filtered to give precipitates, which were confirmed as the crystal form B by analysis of powder X-ray. The suspension was further stirred at room temperature for 14 hours.

Then, the suspension was heated and stirred at 70° C. for 1 hour and at 60° C. for 2 hours. A portion of the suspension was filtered to give precipitates, which were confirmed as the crystal form A by analysis of powder X-ray. The suspension was gradually cooled down to about 9° C. over a period of 7 hours or longer, further stirred at 8° C. for 16 hours and filtered. This was washed with 2-propanol (1.0 L) and dried at 60° C. for 3 hours to give 297.1 g of the crystal form A.

Comparative Example 1

Preparation of the Crystal Form B (1)

To a suspension of 5-[2-amino-4-(2-furyl)pyrimidinyl]-1,2-dihydro-2-pyridinone (2.2 g, 8.65 mmol) in methanol (44 mL) was added sodium methoxide (940 mg, 17.4 mmol) at room temperature under a nitrogen atmosphere, followed by stirring. After 15 minutes, iodomethane was added (1.6 mL, 25.7 mmol), followed by stirring for 22 hours. The reaction mixture was concentrated, and water was added to the residue, and the precipitates were collected by filtration and washed with water to give crude crystals of the title compound (1.98 g). This was suspended in ethanol, and the precipitates were collected by filtration and washed with ethanol to give 5-[2-amino-4-(2-furyl)pyrimidin-5-yl]-1-methylpyridin-2(1H)-one (1.54 g, 66%) as a pale yellow solid (the crystal form B).

Comparative Example 2

Preparation of the Crystal Form B (2)

To 10 g of crude 5-[2-amino-4-(2-furyl)pyrimidin-5-yl]-1-methylpyridin-2(1H)-one (10) were added 10 mL of 2-propanol and 50 mL of water, followed by heating and stirring for about 30 minutes at an external temperature of 85° C. Upon confirming dissolution, the solution was cooled in an ice bath and stirred for 1.5 hours, and the crystals were collected by filtration. The crystals were washed twice with 10 mL of 2-propanol and dried at 60° C. for 10.5 hours to give 6.84 g of the crystal form B.

Measurement of Powder X-ray Diffraction Pattern

Figure 2:
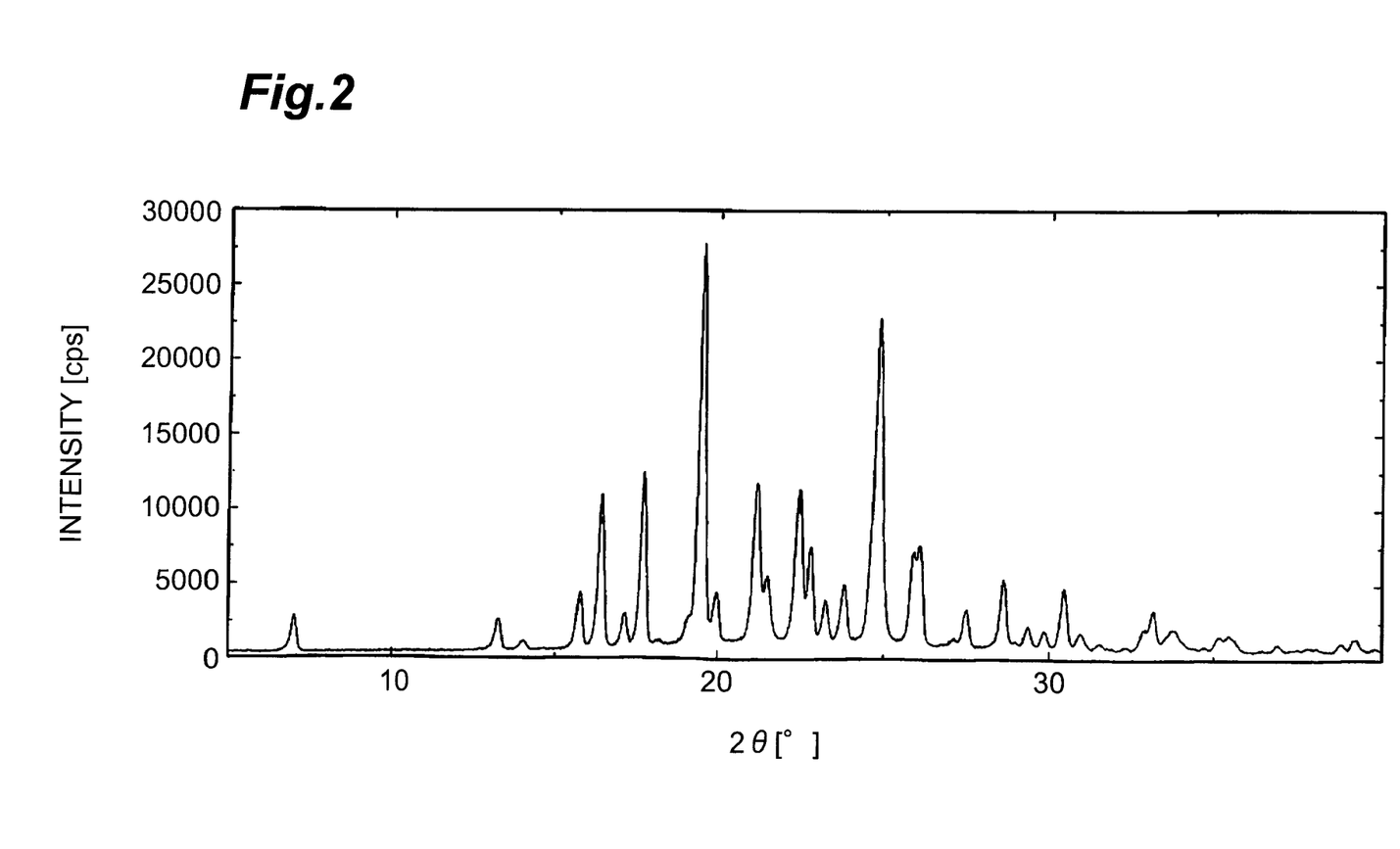
FIG. 2 is a drawing representing a powder X-ray diffraction pattern of the crystals obtained in Comparative Example 1.
Figure 3:
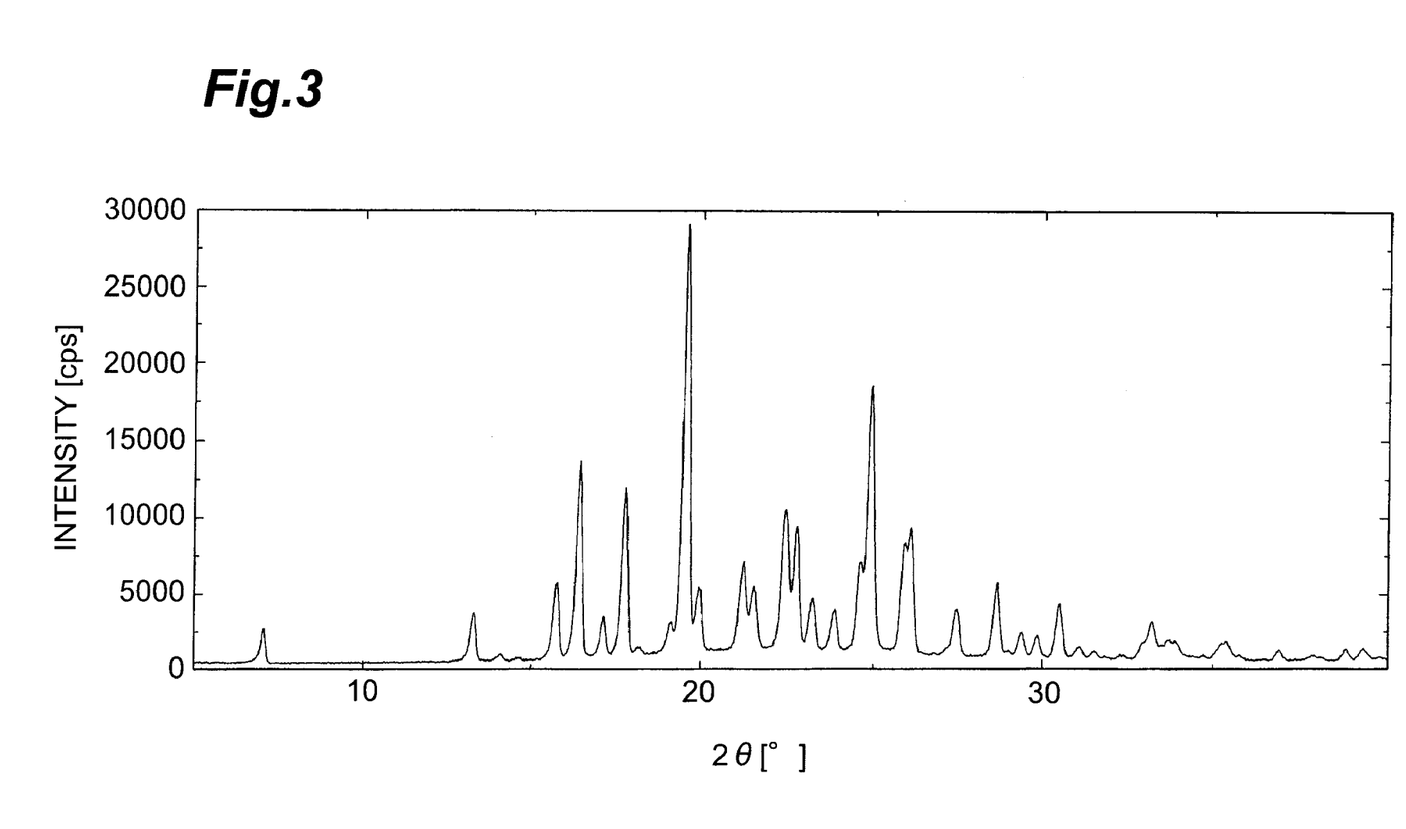
FIG. 3 is a drawing representing a powder X-ray diffraction pattern of the crystals obtained in Comparative Example 2.

The X-ray diffraction patterns of the respective crystals obtained in Example 1, Comparative Example 1 and Comparative Example 2 (the crystal form A, the crystal form B (1) and the crystal form B (2)) were measured under the following conditions. The powder X-ray diffraction patterns for the respective crystals are shown in FIG. 1, FIG. 2 and FIG. 3. Table 1 shows the characteristic diffraction (2θ) peaks for respective crystals.
Target/tube current/tube voltage: Cu/40 kV/200 mA
Monochrometer: Curved crystal monochrometer
Counter: Scintillation counter
Scan speed: 2°/min
Scan step: 0.02°
Scanning axis: 2θ/θ
Scanning range: 5-40°
Divergence slit: 0.5°
Scattering slit: 0.5°
Receiving slit: 0.3 mm

TABLE 1

| Crystal | 2θ (°) |
|---|---|
| Crystal form A | 12.8 |
|  | 18.1 |
|  | 23.5 |
| Crystal form B | 7.0 |
|  | 16.4 |

Measurement of Variable-Temperature Powder X-ray Diffraction Pattern

Figure 4:
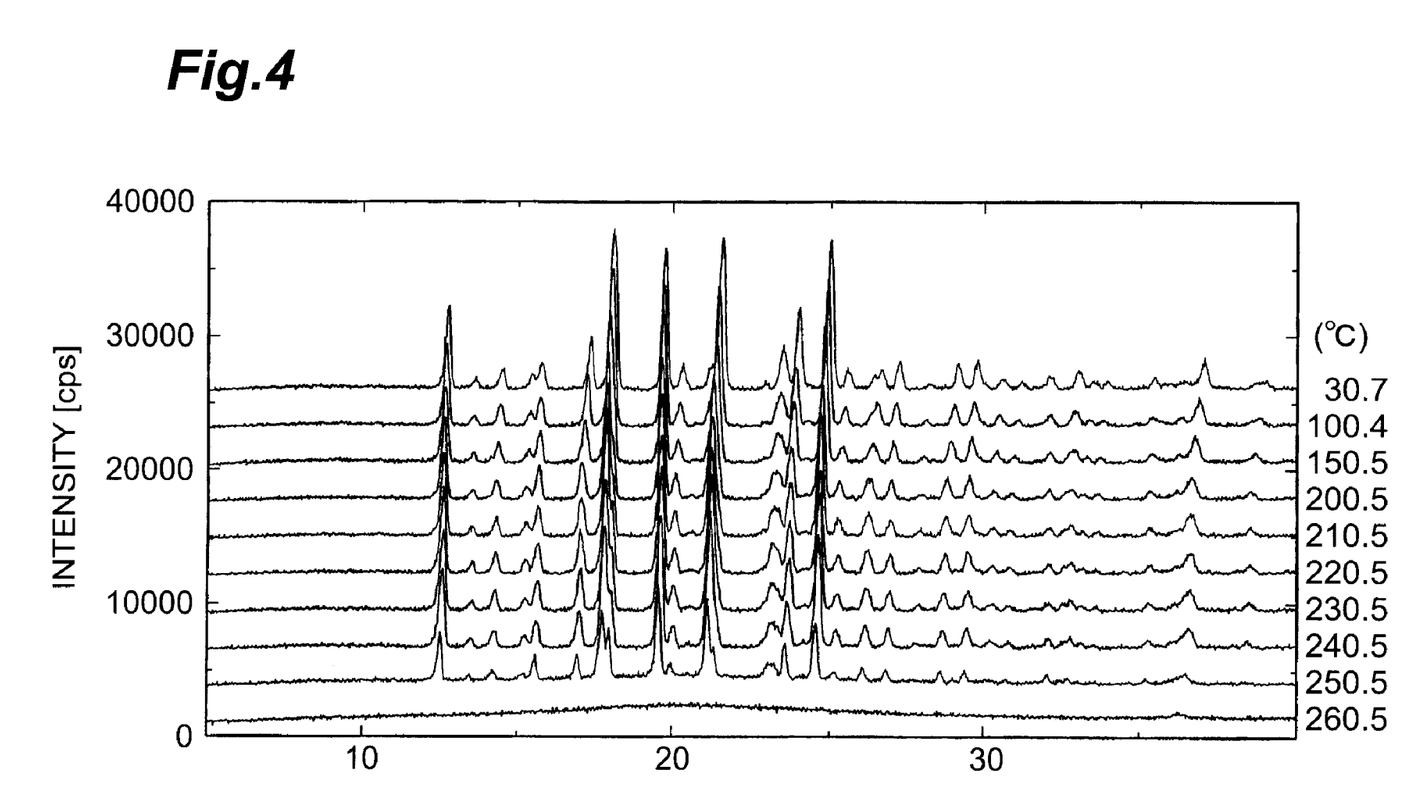
FIG. 4 is a drawing representing temperature-dependent changes of powder X-ray diffraction patterns of the crystals obtained in Example 1.
Figure 5:
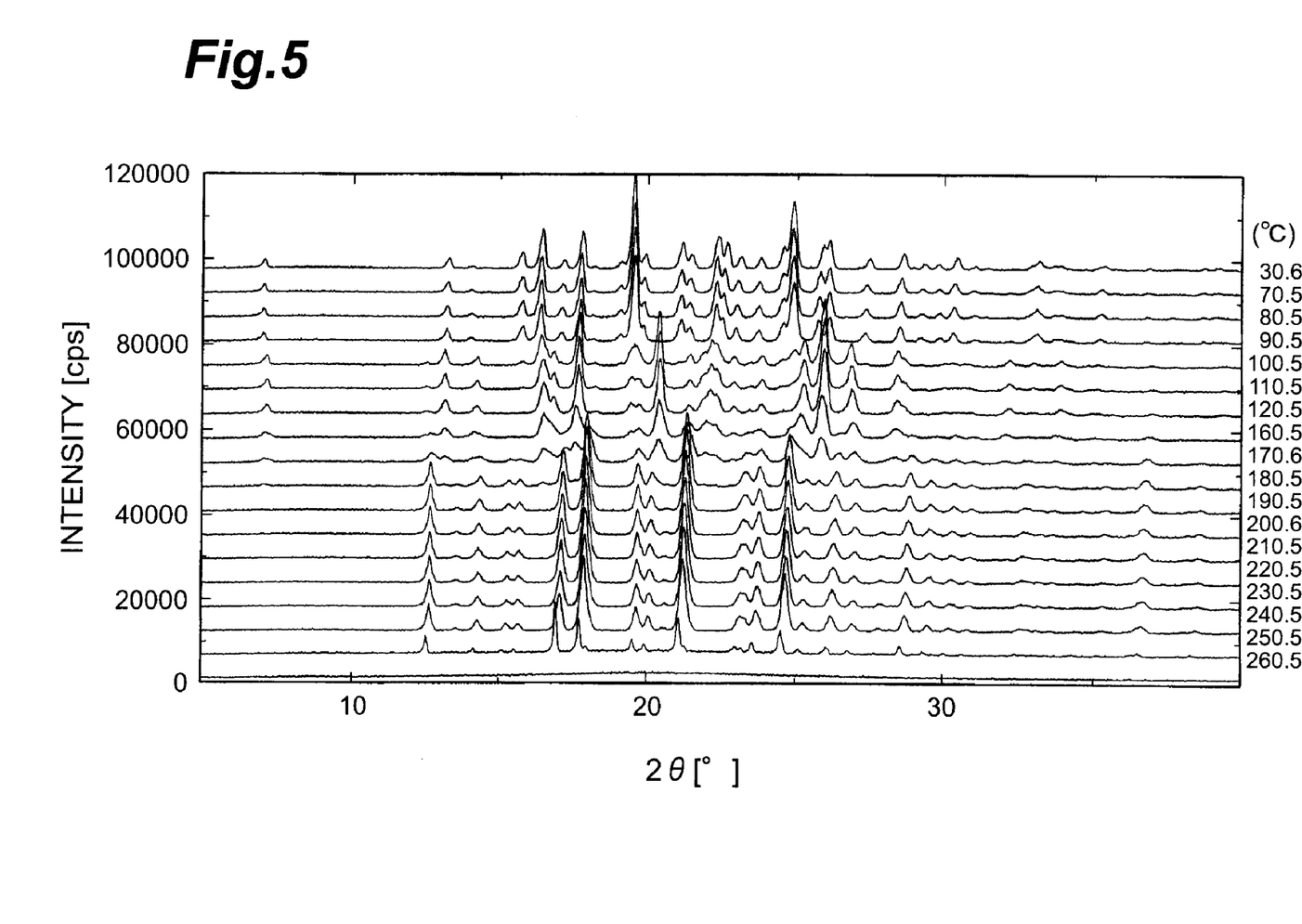
FIG. 5 is a drawing representing temperature-dependent changes of powder X-ray diffraction patterns of the crystals obtained in Comparative Example 2.

Changes in the powder X-ray diffraction pattern, with increase in the sample temperature from 30° C. to 260° C., were observed for the respective crystals obtained in Example 1 and Comparative Example 2 (the crystal form A and the crystal form B). The measuring conditions were the same as for the powder X-ray diffraction pattern measurement described above, except for the measuring temperature. The temperature-dependent changes in the powder X-ray diffraction pattern of the respective crystals are shown in FIG. 4 and FIG. 5.

Thermal Analysis (Differential Scanning Calorimetry; DSC)

Figure 6:
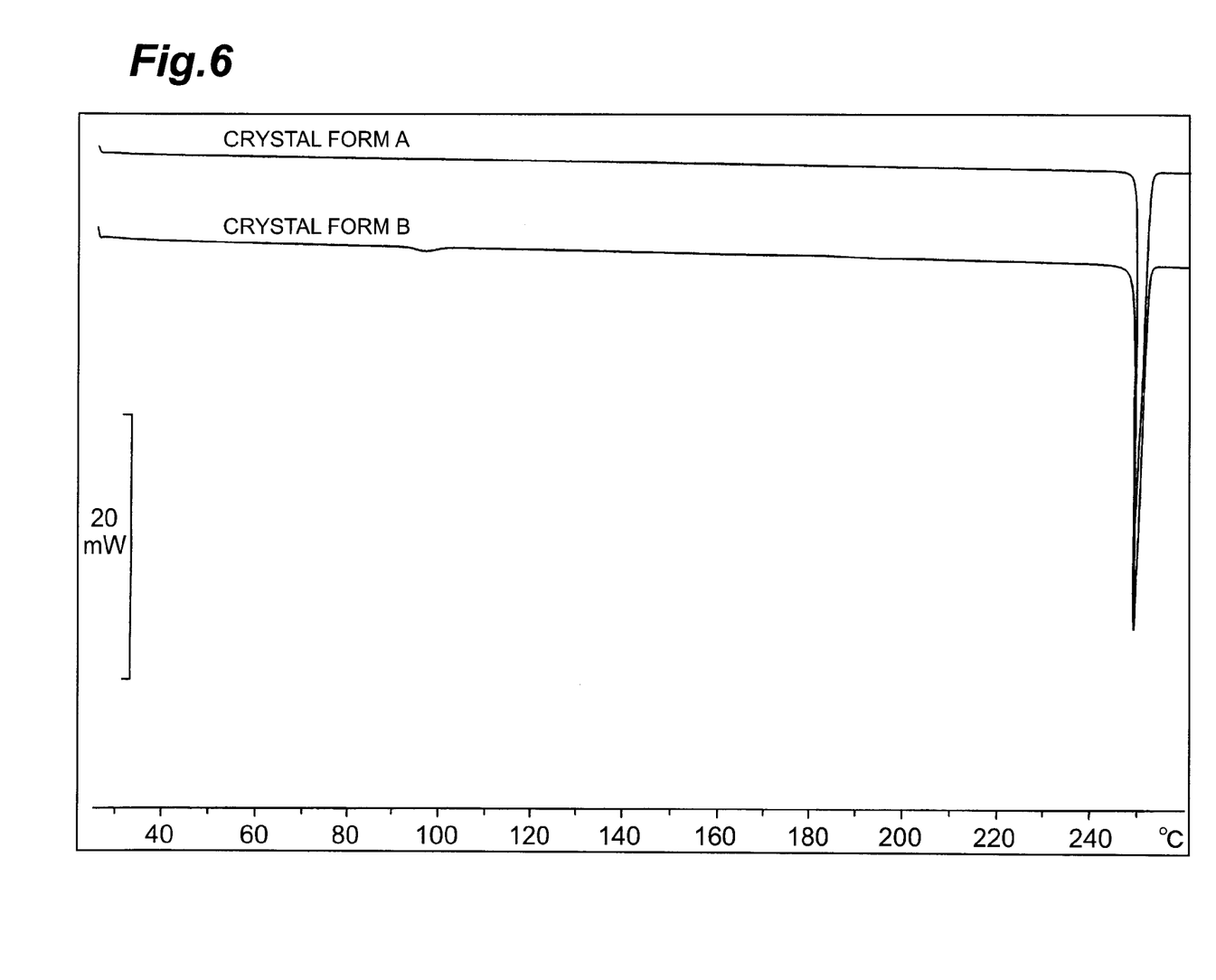
FIG. 6 is a drawing representing DSC patterns of the crystals obtained in Example 1 and Comparative Example 2.
Figure 7:
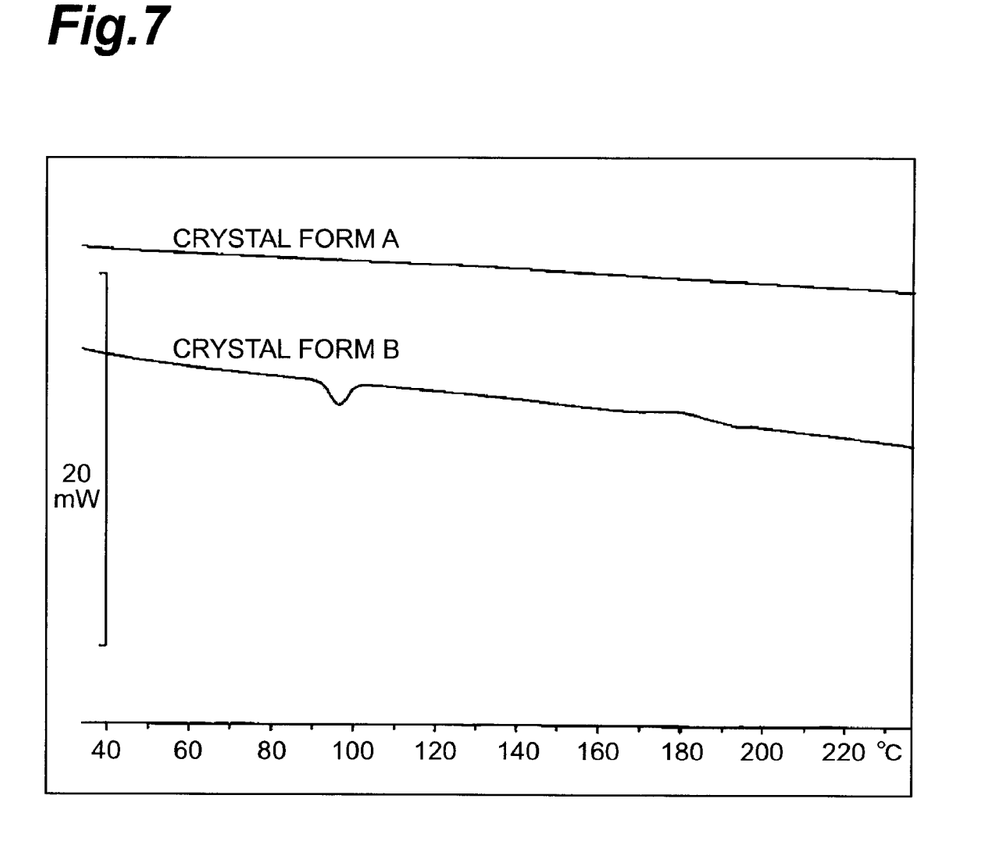
FIG. 7 is a magnification of the DSC patterns in FIG. 6 in a range of 40-230° C.

DSC analysis was conducted under the following conditions, using approximately 3 mg each of the crystals obtained in Example 1 and Comparative Example 2 (the crystal form A and the crystal form B). The DSC patterns of the respective crystals are shown in FIG. 6 and FIG. 7 (magnification of 40-230° C.), and the endothermic peaks and exothermic peaks are shown in Table 2.

Measuring apparatus: DSC822$^e$ by Mettler Toledo
Sample pan material: aluminum
Nitrogen gas flow (40 mL/min)
Start temperature: 25° C.
End temperature: 260° C.
Temperature elevating rate: 5° C./min

TABLE 2

| Crystal | Peak form, onset temperature |
|---|---|
| Crystal form A | Endothermic peak, about 248° C. |
| Crystal form B | Endothermic peak, about 92° C. |
| | Exothermic peak, about 165° C. |
| | Endothermic peak, about 248° C. |

For the crystal form A, no change in the powder X-ray diffraction pattern was seen from 30° C. to 250° C., but disappearance of crystallinity was observed at 260° C. The endothermic peak around 248° C. found by DSC analysis of the crystal form A was shown to have appeared due to melting of the crystals. These results indicated that the crystal form A undergoes no change in crystal form by heating in a range from ordinary temperature to its melting point around 248° C.

For the crystal form B, a significant change in the powder X-ray diffraction pattern was observed between 90 and 100° C. A significant change in the powder X-ray diffraction pattern was also observed between 160 and 180° C., with disappearance of crystallinity being observed at 260° C. The endothermic peak around 92° C. and the exothermic peak around 165° C. found by DSC analysis were shown to have appeared due to these changes in the crystal form. The powder X-ray diffraction pattern also indicated a change to the same crystal form as the crystal form A at 180° C. and higher. These results indicated that the crystal form B transforms to another crystal form (B') at about 90° C., after which it transforms to the crystal form A at about 170° C. and melts at about 248° C. as the crystal form A.

Figure 9:
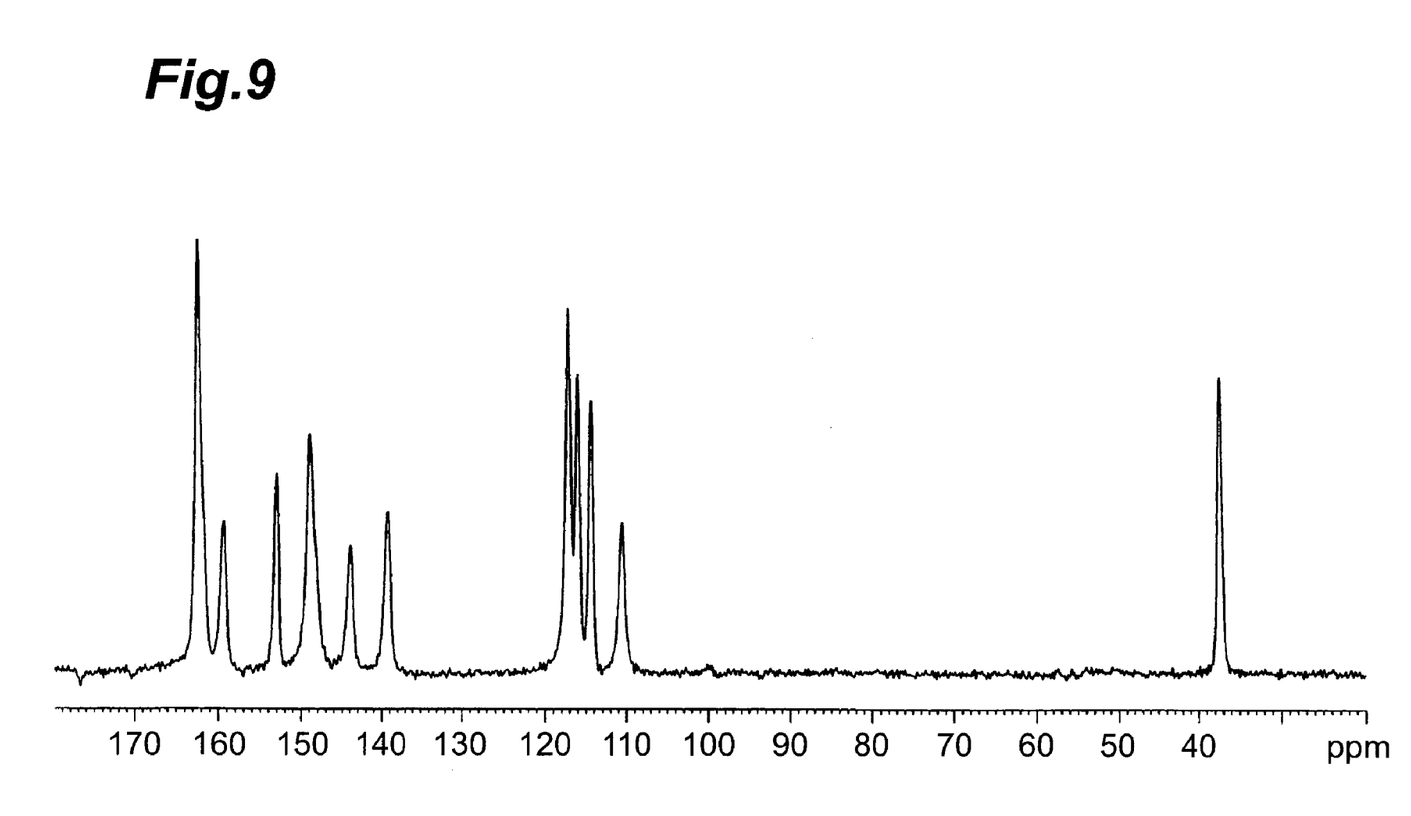
FIG. 9 is a drawing representing a $^{13}C$ solid state NMR spectrum of the crystals obtained in Comparative Example 2.

Measurement of $^{13}$C Solid State NMR Spectrum $^{13}$C solid state NMR spectra of the respective crystals obtained in Example 1 and Comparative Example 2 (the crystal form A and the crystal form B) were measured under the following conditions. The $^{13}$C solid state NMR spectra of the respective crystals are shown in FIG. 8 and FIG. 9. Table 3 shows chemical shifts for the respective crystals. Characteristic peaks in 113.1 ppm and 140.8 ppm were found for the crystal form A, whereas characteristic peaks in 110.6 ppm and 117.2 ppm were found for the crystal form B.

Measuring apparatus: AVANCE 400 MHz (Bruker)
Probe: 7 mm-CP/MAS (Bruker)
NMR cell diameter: 7 mm
Frequency of cell: 6000 round/sec
Measurement method: CPTOSS method
Latency: 10 sec
Contact time: 5000 microseconds
Accumulation: 1024 times
External standard: setting the chemical shift of carbonyl carbon of glycine as 176.03 ppm

TABLE 3

| Crystal form A | Crystal form B |
|---|---|
| 163.6 | 162.5 |
| 161.5 | 159.4 |
| 153.2 | 153.1 |
| 148.1 | 149.0 |
| 140.8 | 144.0 |
| 138.8 | 139.3 |
| 120.0 | 117.2 |
| 119.0 | 116.0 |
| 114.6 | 114.4 |
| 113.1 | 110.6 |
| 37.5 | 37.4 |

Unit: ppm

Measurement of Infrared Absorption Spectrum

Figure 11:
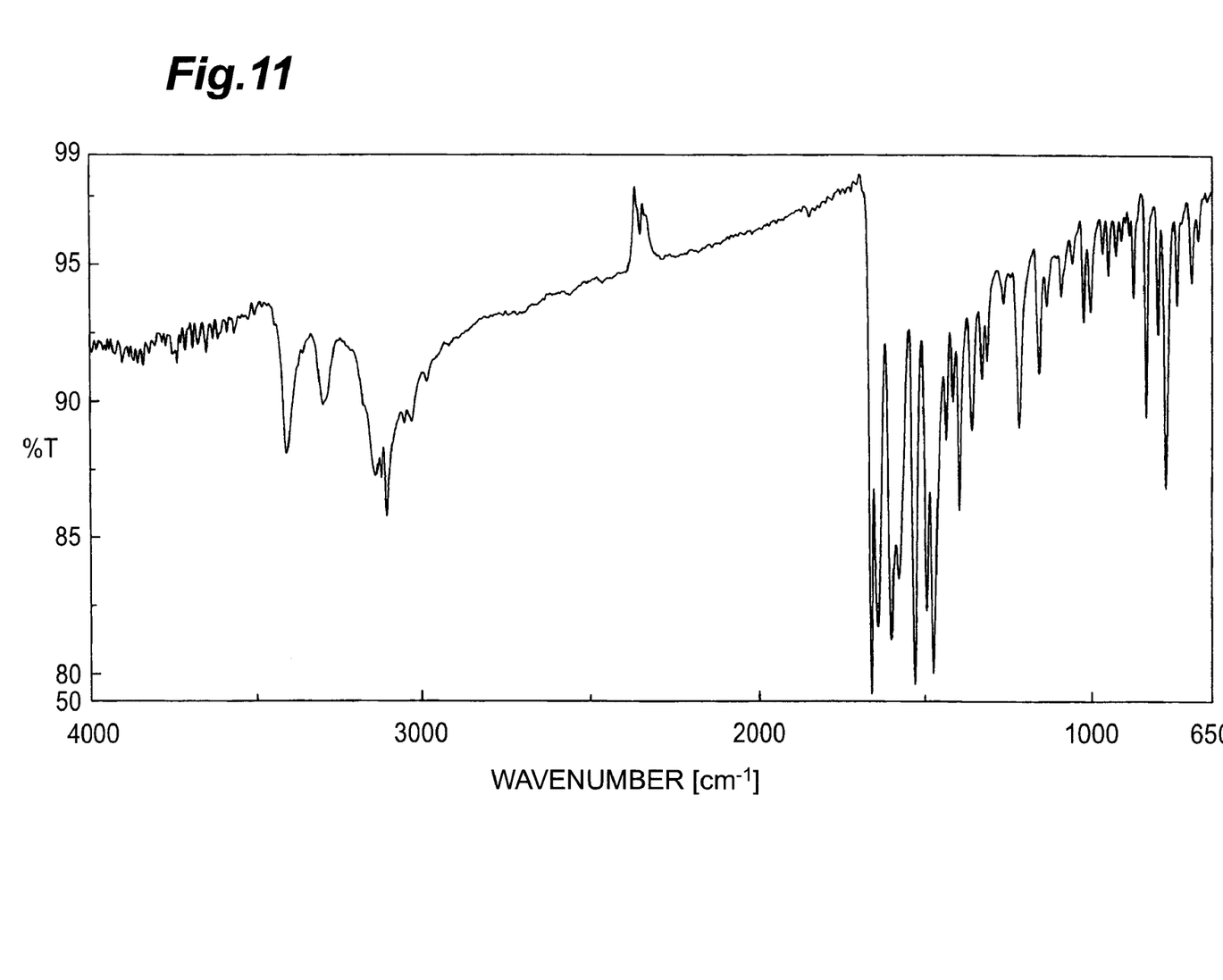
FIG. 11 is a drawing representing an infrared absorption spectrum of the crystals obtained in Comparative Example 2.

Infrared absorption spectra for the respective crystals obtained in Example 1 and Comparative Example 2 (the crystal form A and the crystal form B) were measured under the following conditions. The infrared absorption spectra for the respective crystals are shown in FIG. 10 and FIG. 11. Table 4 shows wavenumber (cm$^{-1}$) of absorption peaks for the respective crystals.

Measuring apparatus: FT/IR-620 (Jasco)
Measurement method: ATR method
Measuring range: 4000 cm$^{-1}$ to 650 cm$^{-1}$
Resolution: 4 cm$^{-1}$

TABLE 4

| Crystal form A | | Crystal form B | |
|---|---|---|---|
| 3322 | 1211 | 3410 | 1156 |
| 3180 | 1156 | 3300 | 1022 |
| 3105 | 1126 | 3102 | 1004 |
| 1662 | 1082 | 1658 | 950 |
| 1607 | 1027 | 1638 | 875 |
| 1568 | 1000 | 1598 | 838 |
| 1530 | 966 | 1529 | 803 |
| 1496 | 948 | 1495 | 781 |
| 1475 | 876 | 1474 | 750 |
| 1432 | 834 | 1436 | 709 |
| 1398 | 806 | 1397 | |
| 1362 | 776 | 1359 | |
| 1319 | 704 | 1329 | |
| 1261 | | 1217 | |

Unit: cm$^{-1}$

Test Example 1

Stability Against Light

The respective crystals obtained in Example 1 and Comparative Example 2 (the crystal form A and the crystal form B) were stored for 1, 3 and 6 months under conditions of 25° C./1000 Lx (apparatus for light stability test; Nagano Science Co. Ltd) and 25° C./dark (control), and impurity contents were measured by HPLC method to investigate stability against exposure to light for the respective crystals. The conditions for HPLC method are shown below. Table 6 shows the obtained results.

(HPLC conditions)
Column: CAPCELL PAK C18 AQ, S-5 μm, 4.6 mm ID×250 mm length (Shiseido, Japan)
Column temperature: a constant temperature around 30° C.
Detection wavelength: 262 nm
Flow rate: 1.0 mL/min
Mobile phase:
Solution A: acetonitrile/water/1M ammonium acetate (10: 1000:1, v/v/v)
Solution B: acetonitrile/water/1M ammonium acetate (900: 100:1, v/v/v)

TABLE 5

| Time (min) | (B) conc. (%) |
|---|---|
| 0 | 10 |
| 20 | 10 |
| 40 | 100 |
| 50 | 100 |
| 50.1 | 10 |
| 70 | Stop |

(Calculation Method of Impurity Content)

The peaks areas of all peaks were calculated from the chromatogram, and the impurity content for each peak (except for the peak of 5-[2-amino-4-(2-furyl)pyrimidin-5-yl]-1-methylpyridin-2(1H)-one) was calculated according to the following formula.

Individual impurity content (%)=(Peak area of individual impurity)/(total of all peak areas)×100

Peaks with impurity contents of 0.05% or greater were recorded as impurity peaks, and their total was recorded as the impurity content of the crystals.

Impurity content (%)=Total of individual impurity contents (%)

TABLE 6

| Crystal | Initial | Storage conditions | Storage period (month) 1 | 3 | 6 |
|---|---|---|---|---|---|
| A | 0.06 | 25° C./dark | 0.14 | 0.12 | 0.12 |
|   |      | 25° C./1000Lx | 0.10 | 0.07 | 0.08 |
| B | 0.34 | 25° C./dark | 0.28 | 0.25 | 0.23 |
|   |      | 25° C./1000Lx | 0.48 | 0.52 | 0.81 |

Unit: %

As shown in table 6, it is clear that the crystal form A is more stable against exposure to light than the crystal form B.

INDUSTRIAL APPLICABILITY

The present invention provides crystals of 5-[2-amino-4-(2-furyl)pyrimidin-5-yl]-1-methylpyridin-2(1H)-one (the crystal form A) which consist of a homogenous crystal form and are excellent in stability against exposure to light and a process for preparing the same. The crystals are suitable for using as an active ingredient of a pharmaceutical composition, particularly a therapeutic agent for constipation.

What is claimed is:

1. A crystal of 5-[2-amino-4-(2-furyl)pyrimidin-5-yl]-1-methylpyridin-2(1H)-one having a diffraction peak at a diffraction angle (2θ±0.2°) of 12.8°, 18.1° and/or 23.5° in a powder X-ray diffraction.

2. A crystal of 5-[2-amino-4-(2-furyl)pyrimidin-5-yl]-1-methylpyridin-2(1H)-one having a peak at a chemical shift of approximately 113.1 ppm and/or approximately 140.8 ppm in a $^{13}C$ solid state NMR spectrum.

3. A process for preparing a crystal according to claim 1, characterized by that 5-[2-amino-4-(2-furyl;)pyrimidin-5-yl]-1-methylpyridin-2(1H)-one is heated and dissolved in a solvent and then crystallized by gradual cooling.

4. A process for preparing a crystal according to claim 2, characterized by that 5-[2-amino-4-(2-furyl)pyrimidin-5-yl]-1-methylpyridin-2(1H)-one is heated and dissolved in a solvent and then crystallized by gradual cooling.

* * * * *